United States Patent
Abraham-Fuchs et al.

(10) Patent No.: US 8,447,552 B2
(45) Date of Patent: May 21, 2013

(54) CONDITIONED MEDICAL TESTING

(75) Inventors: Klaus Abraham-Fuchs, Erlangen (DE);
Karsten Hiltawsky, Schwerte (DE);
Michael Maschke, Lonnerstadt (DE);
Sebastian Schmidt, Weisendorf (DE);
Gudrun Zahlmann, Neumarkt (DE)

(73) Assignee: Siemens Aktiengesellschaft, Munich (DE)

( * ) Notice: Subject to any disclaimer, the term of this patent is extended or adjusted under 35 U.S.C. 154(b) by 585 days.

(21) Appl. No.: 12/318,647

(22) Filed: Jan. 5, 2009

(65) Prior Publication Data

US 2010/0174505 A1    Jul. 8, 2010

(51) Int. Cl.
    *G01D 3/00*    (2006.01)
(52) U.S. Cl.
    USPC ........... 702/108; 702/123; 702/127; 702/179; 702/189
(58) Field of Classification Search
    USPC ...... 702/108, 123, 127–128, 179, 189; 705/2, 705/3, 7.11; 706/10, 62
    See application file for complete search history.

(56) References Cited

U.S. PATENT DOCUMENTS

| | | | | |
|---|---|---|---|---|
| 5,366,896 A | * | 11/1994 | Margrey et al. | 436/48 |
| 5,508,912 A | * | 4/1996 | Schneiderman | 705/3 |
| 5,814,276 A | * | 9/1998 | Riggs | 422/65 |
| 7,606,680 B2 | * | 10/2009 | Okuno et al. | 702/187 |
| 2006/0210435 A1 | | 9/2006 | Alavie et al. | |

* cited by examiner

*Primary Examiner* — Mohamed Charioui
*Assistant Examiner* — Elias Desta
(74) *Attorney, Agent, or Firm* — Harness, Dickey & Pierce, P.L.C.

(57) ABSTRACT

The invention refers to a computer implemented method, a computer system a test machine and a computer program product for executing conditioned and qualified test. An ordering instance may order a set of tests, comprising an initial test and a set of follow-up tests, wherein the execution of each of the follow-up tests is dependent of the result of the respective predecessor test, like the initial test. The conditions for executing the follow-up tests are dynamically definable and are analyzed automatically.

13 Claims, 2 Drawing Sheets

CONDITIONED MEDICAL TESTING

TECHNICAL FIELD

The present invention mainly refers to the field of information technology and medical technology. Particularly, it refers to a computer-implemented method, a computer-implemented system, a computer program product and a test machine, being computer-controlled within a hospital or clinical computerized information system.

BACKGROUND OF THE INVENTION

Usually, clinical facilities comprise of a lot of different clinical departments. For a patient's treatment, typically, an inter-departmental workflow is thus necessary, as different clinical entities have to interact with each other and a clinical workflow between different clinical departments is a very complex task. Therefore, there is a high potential for decreasing cost and increasing quality by improving efficiency of this workflow. The interface between specific departments can benefit very much from intelligent computerized interface systems. Particularly, the radiology department and the central laboratory (shortly: lab) show interdependencies for which an interfacing workflow could be ameliorated with respect to efficiency and also with respect to other parameters, like cost aspects.

In a typical clinical workflow, nowadays, during an initial patient investigation a physician develops a first hypothesis for a possible diagnosis and needs further data in order to support his hypothesis. The strategy in most cases is to start with relatively cheap methods, for example with IVD tests (in vitro diagnostic tests) and to escalate to more expensive methods, for example magnet resonance imaging or the like in a later phase of the diagnostic process.

Typically, the physician orders a set of lab parameters to test his hypothesis. Subsequently, the test is going to be executed in order to gather the lab parameters for the physician. Then, the physician receives the result with the lab parameters and analyzes whether or not this result may confirm his hypothesis. In case that his hypothesis might be confirmed and he needs to have further data, the physician might escalate the workflow in order to get subsequent IVD tests or to initiate diagnostic imaging for gathering more information. In case that his hypothesis might not be confirmed, he has to formulate a new hypothesis and he possibly orders a new set of lab parameters. In this case, subsequently another lab test will be ordered and started.

The above mentioned procedure is time-consuming and error-prone, since the lab tests might be initiated iteratively and a sequence of testing and analyzing is necessary. Therefore, in present systems it may take two or more days for a final clarification of a patients disease, because the initialization of each subsequent step within the clinical workflow requires a written consent of involved medical staff (physician, radiologist, laboratory personal, other specialist etc.).

DESCRIPTION OF PRIOR ART

In present prior art systems, process steps being related to a first department are normally being executed isolated from and independent of process steps, being related to a second medical department. There is a chain of personal decisions from the respective physicians. Particularly, each laboratory test needs to be ordered or confirmed by the physician. Automated software support is only used within local devices, but not within an inter-departmental workflow and thus, not across the interface of hospital departments.

US 2006/0210435 discloses a method for automatically analyzing an executed laboratory test. However, this system is only to be used within the laboratory department and could not be used for communication with other departments and clinical institutions.

Therefore, there is a need for an automated support system for a decision taking with respect to laboratory tests and follow up laboratory tests and generally with respect to a test workflow.

SUMMARY OF THE INVENTION

Abstractly stated, the present invention is a computer-implemented method and system that allows for an optimization of a clinical test workflow with respect to efficiency. Particularly, the present invention allows for a conditioned testing, wherein a result of the respective test is analyzed. Based on this analysis there is a decision already within the testing laboratory department whether or not to initiate a follow-up test.

In the following the present invention will be described with respect to the method. Any aspects, features or advantages mentioned in this respect might also be applied to the other categories of the claims (for example to a system according to the invention and also to the computer program product according to the invention). With other words the system and the product might also be adapted to incorporate features, having been mentioned with respect to the description of the method according to the invention. Any functional feature refers to an apparatus feature, having the respective functionality.

For example the step of "receiving an order" refers to a "reception unit which is adapted to receive orders and interfaces with other (ordering) departments". Further, the step of "executing the received at least one test" refers to a structural entity of the apparatus, which is used as "execution unit" for executing the test, wherein the execution unit may be arranged within or integrated in a test machine.

Particularly, the present invention refers to a computer-implemented method for implementing a set of tests, comprising the following steps:
- receiving an order for at least one test;
- automatically executing the received at least one test;
- receiving a result of the executed at least one test;
- analyzing the result in order to determine whether at least one follow-up test needs to be executed and if yes:
  - automatically generating an order for the at least follow-up test and iteratively executing the steps for the at least one follow-up test.

In the following, there is given a short explanation or definition of terms, used within this disclosure.

"Implementing" a set of tests is to be construed in the sense of generating or establishing an information technological clinical process, which might comprise a plurality of testing steps. A clinical test usually consists of a sequence of testing steps or test elements and might be controlled by a clinical workflow. Sometimes different process elements might be executed subsequently or in parallel. Each process step within the test has to be linked to other process steps and, thus, show interdependencies. Further, interdependencies also exist with respect to other clinical departments. For example, depending on the result of an image acquisition process within a clinical department, different clinical tests have to be initiated.

It is contemplated that the method and the system of the present invention is suitable for implementing a set of clinical laboratory tests. However, the invention is not limited to laboratory tests and it also might be applied to other clinical processes within a clinical workflow or taskflow, like image acquisition processes, administrative processes, for example, with respect to a scheduling of relevant devices like imaging acquisition modalities, administrative processes with respect to clinical personal, processes within different clinical departments, cost related processes, billing systems etc. Usually, there is not only one single test, but a set of tests that has to be carried out.

The "order" for a test might be generated manually and might exist in paper form or, preferably, might be generated by means of a computerized tool and might be confirmed by a respective confirmation signal by the physician which might be forwarded to the laboratory department. Typically, the order consists of a set of testing parameters. These parameter refer to testing conditions, information and meta-information with respect to the specific patient, time information, etc. One of several major aspect of the present invention is to be seen in that the order may also comprise rules. The rules may refer to specific testing conditions and to the result of the test which might serve as a basis for possible follow-up tests. Abstractly stated, for example following order might be given:

"order for test A: in case the result of test A is "−"→no further testing; in case the result of test A is "+"→executing a follow-up test B".

Thus, there could be a cascade of tests, wherein the result of an earlier or predecessor test is the basis for the decision with respect to follow-up actions or with respect to the execution of a follow-up test.

According to one aspect of the present invention there is a conditioned testing. In case the presumptions for a follow-up test are given, this follow-up test is initiated and executed automatically. No further interaction with the ordering instance (the ordering physician etc.) is necessary anymore. The physician, however, might still be informed about the result and about the decision for follow-up testing. This leads to the advantage of efficiency enhancement and failure reduction.

According to one aspect of the present invention receiving the result of the executed test is done within the testing department. Additionally, the result of the executed test might also be forwarded to the ordering instance, i.e. to the radiology department or any other department within the clinic. However, this forwarding is not necessary anymore for the execution of follow-up tests. Also, analyzing the result of the test is also done within the testing department. Usually, analyzing the result of the test comprises receiving the result, comparing the result with given (pre-determined or user set) rules, values or parameters. Analyzing further might comprise an access to one or different databases, for example relating to diagnostic devices or imaging modalities within the hospital, relating to scheduling of devices, to availability analysis, to cost related aspects, to a billing system and/or relating to clinical guidelines. Analyzing automatically generates a decision whether or not to initiate a follow-up test. In case a follow-up test needs to be executed an order for a follow-up test is generated automatically and the steps of the method mentioned above are carried out again for the follow-up test. Thus, there might be a sequence or a cascade of tests and follow-up tests, wherein the execution of a test depends on the result of a specific predecessor test.

Analyzing particularly comprises an access to a rule database. In the rule database there are stored rules with respect to the specific tests, to the result of the tests and to possible follow-up actions with respect to these results or to conditions for executing follow-up tests. In a preferred embodiment analyzing also could comprise the step of notifying a user about possible inconsistencies with clinical guidelines or with other clinical knowledge. This might be the case, if a test is ordered although it might not be indicated due to general clinical guideline knowledge.

According to a further aspect of the present invention analyzing further comprises notifying the user about the result of the test. This notification might comprise additional information in case the test says that certain standard values are not given. For example the user might be notified about an extension of certain limits, for example "blood pressure too low" or "blood pressure too high". These notifications might be sent to other instances within the clinical workflow in order to inform about the test result.

According to one of the key aspects of the present invention the result of the test is analyzed with respect to further testing actions, i.e. for initiating of a follow-up test. Thus, there might be implemented a conditioned workflow of testing, wherein the condition is analyzed automatically and wherein a further testing (follow-up testing) is also initiated and executed automatically, without the necessity of interaction with the ordering instance. However, according to an alternative embodiment the execution of a follow-up test is dependent of a confirmation signal of an ordering instance. In the latter case the method automatically generates a suggestion for a follow-up test, wherein the execution of this suggested follow-up test is only executed in case a confirmation signal has been received. In any case, however, the suggestion for follow-up actions (like one single follow-up test, a sequence of a follow-up tests, a further user interaction, a patient's interview or other actions) is generated automatically. A method according to the present invention might be executed iteratively for all tests and follow-up tests.

According to a preferred embodiment of the present invention the test and/or the follow-up test might be based on different clinical departments. For example a first test might relate to a laboratory test, whereas a second test might relate to an image acquisition within the radiology department. Thus, according to the present invention a workflow might be automatically generated that relates to different clinical departments.

According to a further aspect of the present invention the test and/or a follow-up test might be based on the same or on different test samples. According to a preferred embodiment the same sample is used for the test and for all of the follow-up tests, if possible. This has the advantage, that it is only necessary to take one blood sample of the patient. However, it might also be the case, that a follow-up test needs to be carried out on a further sample. In this case the respective notification for the medical staff is generated automatically.

According to yet another aspect of the present invention analyzing the result is based on aspects, selected from:
the received result of a predecessor test or other earlier tests;
medical meta-information;
medical knowledge, definable in rules;
user input
context situation.

As already mentioned above, analyzing might comprise a database access to look-up predefined parameters, compare values or guideline specifications.

According to a further aspect of the present invention the steps of the computer-implemented method might be executed iteratively. This means that in a first session there is received an order for an initial test; this initial test will be executed automatically; the result of this initial test is received and analyzed within a test unit itself in order to decide if a first follow-up test for the initial test is necessary or not. In case a first follow-up test is necessary, there is generated an order for the first follow-up test. Then, this first follow-up test is executed automatically as second action. In case the result of this first follow-up test leads to another second follow-up test, also this (second) follow-up test will be executed automatically. After each execution and analysis of the respective result there might be an automatic initiation of a possible third follow-up test and so on.

According to a preferred embodiment a user might interrupt this automatic execution of tests and follow-up tests by a respective interruption signal. According to another embodiment of the present invention the follow-up tests are not executed automatically, but they are only executed after having received a user confirmation.

According to another aspect of the present invention the workflow for the set of tests might be dynamically structured. For example it might be possible, that a user defines time-related parameters for the execution of the test and/or the follow-up tests. For example the user might set that the follow-up test needs to be executed immediately after having received an order of the follow-up test. Alternatively, the user might define that a follow-up test is only to be executed under certain preconditions or circumstances. For example it might be set that each follow-up test is only to be executed after a certain preparation phase. The time-related parameters and the time schedule are dynamically adaptable.

According to another aspect of the present invention the test and/or the follow-up test might be executed subsequently or—if possible—in parallel. A parallel execution of different tests might be implemented if there were more than one testing device for the same test or if different tests had to be carried out.

In case a further sample for a follow-up test needs to be taken, a respective user notification will be generated automatically.

Preferably, the result of the test and/or the follow-up test and the result of the analyzing process are stored in a storage medium, i.e. a data base, related to the testing device or in a central storage.

According to another aspect of the present invention also statistical information is gathered, so that this statistical information might be used for next tests. For example, the statistical rule might be: "After execution of test A, in 95% of cases follow-up test B will be initiated". This statistical information might be used and accessed during analyzing the result of the respective test and for generating an automatic suggestion for next actions to be taken.

According to further aspect of the present invention it is not necessary that a physician inputs an explicit order for a test. Alternatively the order for the test might be deduced, based on a user input. The user input might be a hypothesis, an alternative hypothesis, a clinical question, or any other more abstract input information. Based on the received input, an order for the respective test will automatically be deduced. The deduction of the respective test is based on a rule database. For example the rule database might comprise a certain clinical question and a set of clinical tests to be carried out in order to answer the clinical question.

According to yet another aspect of the present invention the method implements an event-based or result-based workflow of tests, wherein the test is dependent on a result of the respective predecessor test or is dependent on an analysis of the respective predecessor test.

Thus, there is provided an intelligent software tool with improved connectivity between different clinical departments, in order to minimize the number of separate action items within the clinical workflow. Further the clinical workflow might be optimized with respect to time-related aspects and/or with respect to cost-related aspects or in relation to any other pre-definable parameters.

For example in case an ordering physician orders are specific lab test the invention proposes the following situation: Instead of sending the result of the lab test (or of any other test machine) back to the ordering physician the laboratory test is automatically analyzed within the laboratory device according to the present invention. This is a significant enhancement as, in most of the cases, a next action step might directly and automatically be derived by the laboratory system itself or by the treating physician in advance (before ordering the first lab test). According to the invention in most of all cases the treating physician needs not to interpret the result of the tests and needs not to decide manually for the next action step. This is executed automatically or semi-automatically, supported by a computer system according to the present invention.

According to the invention there exist two mechanisms which might be used separately or in combination of each other.

According to the first mechanism the lab system has access to a patient history and to previous diagnostic findings of the patient via connectivity to electronic patient record data in the HIS (Hospital Information System). As mentioned above according to the present invention the result of the test is analyzed automatically. Further, the result might be compared with other patient-related data, electronic patient records and with other statistical information in order to automatically derive the most optimal next diagnostic test step. The suggestion for the most optimal next diagnostic test step is generated and outputted. Preferably, this next test action which has been analyzed as being most optimal in the actual situation is initiated automatically.

According to the second mechanism the ordering physician delivers in addition to an ordered parameter set the actually preferred hypothesis plus alternative hypothesis. Based on the result of the test, the system according to the invention automatically develops a strategy how to confirm the first hypothesis, being given by the physician. In case the first hypothesis is disproved, the alternative hypothesis is analyzed. In case further user interaction is necessary, the user is notified with a respective message over the user interface.

As already mentioned above, the physician might explicitly input an order for a test. Alternatively, the physician might input a fixed set of lab parameters, to be tested. This might be done within a graphical user interface and a respective representation of a set of possible test parameters. The user then selects specific parameters out of the represented set of parameters. Further, alternatively, the physician does not need to input a fixed set of lab parameters, but poses a clinical question like "Inflammation Assessment" to the lab department and leaves it to the expert system according to the present invention to automatically determine the best set of lab parameters to be investigated for answering this clinical question. This assessment might be done by accessing a rule database. The assessment is then carried out automatically.

According to a further aspect of the present invention the treating physician does not input only one test, which has to be executed and analyzed according to the present invention, but he inputs a set of tests. Further, he may input conditions for analyzing the result of the test and/or for executing follow-up tests. Thus, the treating physician is able to already order at least one subsequent testing depending on the result of the initial or predecessor test (for example a Troponin test and a subsequent CK-MB follow-up test in case "Troponin is high").

According to another aspect of the present invention an alternative reimbursement model might be introduced. In present state of the art systems there is a one-to-one relation between ordered lab parameters and incurred costs. Instead of this one-to-one relation, the costs and the payment might be related to the answer of a diagnostic hypothesis only and the laboratory department decides by itself what set of subsequent laboratory tests have to be executed to answer the question. For a more detailed cost breakdown scheme the way towards a final establishment of a diagnosis might be described by a decision tree containing several levels of subsequent decision nodes and wherein the reimbursement is based on a "fee per progress" along the levels of the decision tree. This reimbursement can be implemented with the health care insurances, but also for internal purposes within the hospital.

According to a further embodiment the method according to the invention might be extended by an optimization module. The order of tests is decided on diagnostic relevance versus cost related aspects. Further, the decision might be based on statistical values and might be combined with a risk percentage or what is the confidence level of the results of the respective tests. The optimization parameters might be definable. In case of conflicts with respect to optimization parameters, there could be defined specific rules. For example the clinical result should overrule the cost decision in case of conflicts.

As an advantage an effectiveness of the method according to the invention may be measured automatically. Further, it is possible to give a cost estimation for all tests and also for tests which are planned to be ordered, already in an early stage beforehand. Therefore, the physician gets an overview of the costs incurred beforehand. Further, the costs incurred with the old testing scheme according to the state of the art might be compared to the costs, incurred with the testing scheme, being optimized according to the present invention.

As all data is stored, a monitoring of the method according to the present invention is possible. Further, this (statistical) knowledge (for example in most of all cases follow-up test B is executed after initial test A has been carried out) might be fed back to the system again so that the expert system is able to learn. Further, clinical guidelines might be adapted according to this knowledge.

According to another aspect the present invention relates to a computer-implemented system for implementing a set of tests. The system comprises a reception unit, an execution unit, an analyzing module and an iteration unit. The system interacts with the different clinical departments, i.e. with the laboratory department and with radiology. Further, the system has a user interface for inputting and outputting data.

In a preferred embodiment the computer-implemented system is an expert system. Preferably, the analyzing module of the system is directly integrated into an automated IVD-Analyzer or into another test machine, so that the decision for follow-up tests can be made before the blood sample leaves the analyzer with very low costs, compared to a state of the art workflow, where the sample first is transported into a storage area and then put back into the analyzer for repeated testing, in case the physician orders a follow-up test.

According to another aspect the present invention is related to a test machine for executing clinical tests, comprising a test module, which is adapted to execute the method for implementing a set of tests, which has been described above. The execution unit might be integrated into a test machine (modified according to the present invention) or might be provided as add-on module for conventional test machines or analyzers, respectively.

As mentioned above, according to a preferred embodiment the system is realized as an add-on module, which might be switched on to existing test machines or analyzers in the laboratory department. The system provides a further functionality for testing, so that also a conditioned testing and a workflow for a sequence of tests might be definable and executable automatically.

According to yet another aspect of the present invention the system on-line calculates the cost efficiency of follow-up tests, based on a database, relating to costs and based on experiences from former tests. If, for example, the costs for getting a sample back from storage is 5 Euro and the costs for follow-up testing is 1 Euro and the likelihood that a follow-up test is ordered in this special case has been 50% in the past, the suggestion would be that it is most cost efficient to do the follow-up test directly in the analyzer instead of waiting for an additional order for the follow-up test from the ordering physician.

According to another aspect the present invention refers to a computer program product or a computer program having computer executable instructions for executing the method, mentioned above, if that program is loaded onto a computer, wherein the method is adapted for implementing a set of tests. The computer program product or the program might be stored on a computer-readable medium.

DETAILED DESCRIPTION OF THE DRAWINGS

Embodiments of a method of the present invention are described hereinafter. In the following description, meaning of specific details is given to provide a thorough understanding of embodiments of the invention. One skilled in the relevant art will recognize, however, that the invention can be practiced without one or more of the specific details, or with other methods, modules, entities etc. In other instances, well-known structures, computer related functions or operations are not shown or described in detail, as they will be understood by those skilled in the art. Also, it will be understood that the steps of the method have not necessarily to be executed in still the same order possibly might be executed in a different order if technically possible. Further, not all steps of the method need to be executed on the same computer (module) Accordingly, some steps of the method might be executed on the same or on other modules.

Further, the method is described with respect to medical testing. However, it is apparent that also other actions or any other kind of patient's treatment or medical data processing might also be applied and processed, respectively.

Reference throughout this specification to "one/an embodiment" means that a particular feature, structure or characteristic described in connection with the embodiment is included in at least one embodiment of the present invention. Thus, the appearances of the phrases "according to one embodiment" or the like in various places throughout this specification are not necessarily all referring to the same embodiment. Furthermore, the particular features, structures or characteristics may be combined in any suitable manner in one or more embodiments.

Figure 1:
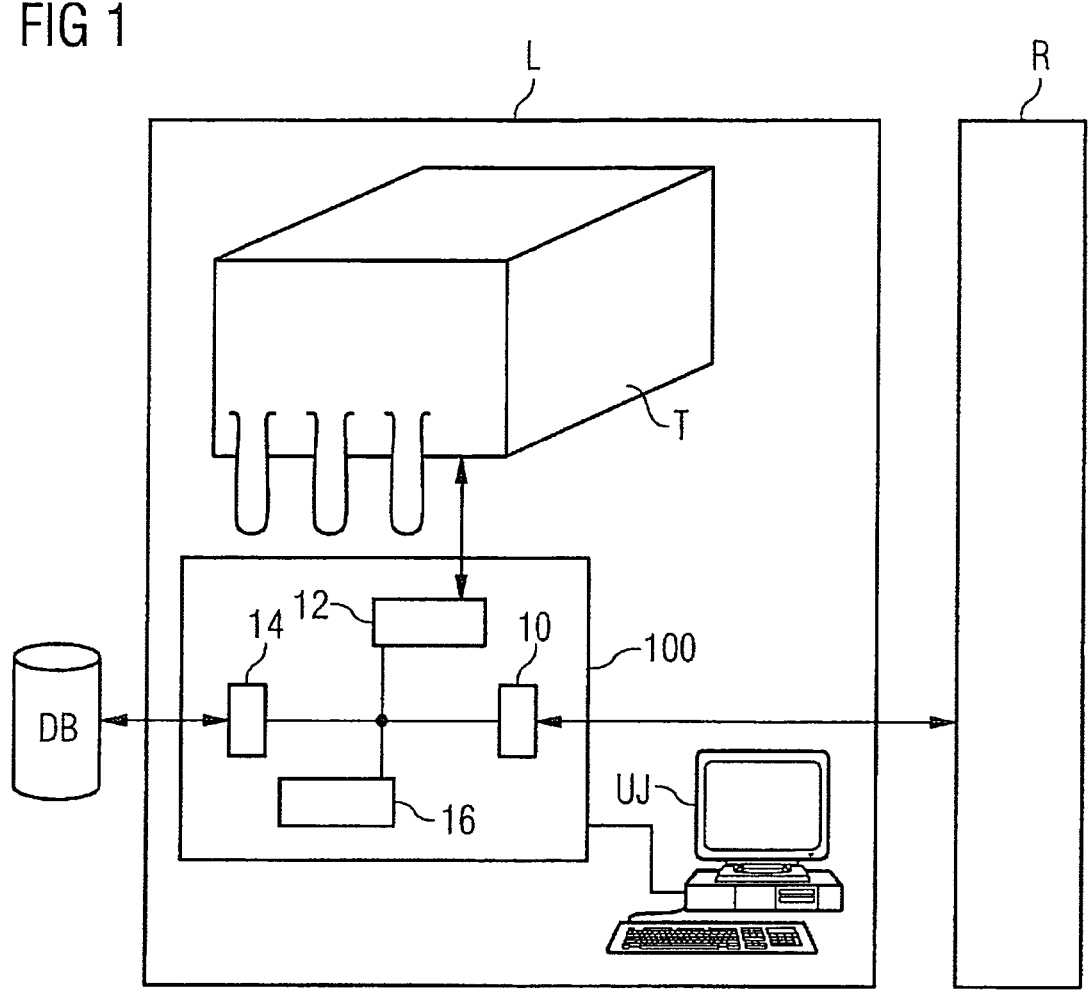
FIG. 1 is a schematic overview of an example of a system according to the present invention and according to a preferred embodiment and FIG. 2 is a flowchart according to a preferred embodiment of the method according to the present invention.

FIG. 1 shows a schematic overview of the context for a system 100 of the present invention according to a preferred embodiment. Different clinical departments interact with each other. In this case the radiology department R interacts with the laboratory department L (shortly: lab). In other embodiments, also other departments are involved in this interaction. Possibly, an administrative unit or any other units may be combined into this interaction. As can be seen in FIG. 1 the lab L comprises a test machine T which is adapted to execute laboratory tests, which have been ordered by an ordering instance, which in the example in FIG. 1 is the radiology. Test machine T might comprise a carousel with respective recesses for engaging with sample bottles or alternatively might be any other kind of testing assembly. The ordering instance for the respective test might be the laboratory L itself or might be any other department, like oncology, which has a respective interface with the laboratory L.

In contrast to the state of the art systems the present invention provides an automated order system for clinical tests, wherein a qualified and conditioned ordering might be selected. For this reason a system 100 is connected ahead or at the input of the test machine T. The system 100 has a testing interface to the test machine T (which in FIG. 1 is depicted by a vertical arrow between tester T and execution unit 12 of system 100), an input interface with other departments (which in FIG. 1 is depicted by an arrow between radiology R and reception unit 10 of system 100) for receiving an order for the test and possibly also might have a user interface UI and an access to databases DB.

Generally, the specific use and application of the test machine T might vary or might be coupled (connected via internet or intranet) to other testing machines. For example, a first test machine might be adapted for blood testing, liquid testing, blood pressure testing and/or blood sugar testing, a second test machine might refer to liver testing whereas a third test machine might be directed to an image acquisition with different modalities, like MRT, CT or ultrasonic image acquisition etc. In FIG. 1 a test machine T is depicted with test tubes for receiving and analyzing samples for an IVD testing.

The system 100 preferably is computerized and comprises a set of units, which themselves might be implemented as software modules or as hardware modules as well or as a combination thereof. The system 100 comprises a reception unit 10, an execution unit 12, an analyzing module 14 and an iteration unit 16.

In FIG. 1 an example of the system 100 is depicted, in which all units 10, 12, 14, 16 are provided within the system 100. However, it is also possible that at least one of the units 10, 12, 14, 16 is provided as external instance which communicates with the system 100 over a respective interface. In FIG. 1 the database DB is depicted as external instance which might be accessed by the analyzing module 14 of the system 100. In an alternative embodiment it is also possible that the database DB is part of the system 100.

The reception unit 10 is adapted for receiving and/or placing an order for the test from/to an ordering instance, which might be the radiology department R. In a first embodiment the reception unit 10 itself has the interface to the radiology department R, whereas in a second embodiment the system 100 has the interface to the radiology R.

The execution unit 12 is adapted for automatically initiating the test, which has been received by the reception unit 10. Therefore, the execution unit 12 has an interface to the test machine T or it is integrated into the tester T. Preferably, the input interface of the system 100 and the testing interface to the test machine T are adapted for transmitting parameters for testing. These parameters might concern context parameters which are relevant for testing. For example parameters might be volume of the sample, testing conditions like temperature, standard values, contrast parameter values, and any other meta-information which might be relevant for execution of the test. The execution unit 12 is further adapted to automatically start the respective test on the test machine T, after having received the order for the test via the input interface. In the preferred embodiment no further user interaction is necessary anymore. Alternatively, the testing on the test machine T might be initiated semi-automatically. In the latter case a user confirmation signal, which might be inputted over the user interface is necessary for executing the test on the test machine T. In this case the user gets an additional possibility to control the testing process.

After the test has been executed on the test machine T the result of this test is sent via the test interface to the system 100 again. The analyzing module 14 is adapted for receiving the result of the executed test and analyzes the result. Preferably, analyzing might be adapted dynamically for specific testing context situations. Preferably, analyzing is done in order to determine whether at least one follow-up test needs to be executed or not. Analyzing does not necessarily require a user input and also might be executed automatically. Analyzing might further comprise an access to the database DB, for example, for comparing the test result with specific standard values. Moreover, analyzing might also access specific data which have been transmitted via the input interface from the ordering instance R. Possibly these parameters indicate that the ordering instance wishes a follow-up test to be executed. The order for a follow-up test might be generated during generation of the order for the test itself or also might be generated afterwards. This aspect is a major advantage over present state of the art systems, as at least one follow-up test (there might be generated several follow-up tests for one initial test), might be generated already during ordering the first (initial) test. This also is a major advantage over known systems as a recirculation of the sample is not necessary in case a set of tests have to be carried out on the same sample. Efficiency, therefore, might be ameliorated significantly.

However, according to a preferred embodiment it is not necessary that a follow-up test order is already generated by the ordering instance R during generation of the test order itself. Particularly, the follow-up test order might also be generated automatically by the system 100 itself. For this reason the analyzing module 14 and the iteration unit 16 interact with a rule database (not shown in FIG. 1) for deducing possible follow-up test orders. For example the rule database might comprise rules like:

"If testing is 'leucocytes' and 'test result is not within standard values'→'follow-up test needs to be executed for testing blood sugar'".

The rule database might be dynamically adaptable according to actual medical knowledge. Further, the rule database also might access statistical values. Statistical values, for example, might indicate that in 80% of the case a follow-up test for "blood sugar" is executed after having executed the tests "blood cells" or "blood coagulation". Also this statistical values will be considered by analyzing whether or not a follow-up test needs to be executed.

In case a follow-up test turns out to be necessary, a respective order for a follow-up test will be generated and sent to the execution unit 12 for automatically initiating the follow-up test on the test machine T.

The iteration unit 16 is adapted for automatically generating an order for at least one follow-up test, in case such a follow-up test needs to be executed. The order for the follow-up test then will be forwarded to the execution unit 12 to be transmitted to the test machine T.

Preferably, the system 100 according to the present invention may be implemented in any suitable network system, like client-server systems, local area networks, wide area networks or alternate types of internet work. Moreover, anyone of a variety of client-server architecture may be used, including but not limited to TCP/IP(HTTP-network) or specifications like NAS or SAA. All modules and units of the system 100 may be interconnected by a bus system. Further, there might be used a central or several databases DB for storing and retrieving data related to the implementation of the testing process. Thus, the network may include a plurality of devices, such as a server, routers and switching circuits connecting in a network configuration, as known by a person skilled in the art.

The user of the system 100 may use a computer device, such as a personal computer, or a personal digital assistant or any other computerized devices for interacting with the system 100. Access to other network modules and servers might be executed by using wireless or wired communication protocols. The computer device might be coupled to I/O-devices (not shown in FIG. 1) that may include a keyboard in combination with a pointing device, such as a mouse to input data into the computer, a computer display screen and/or a printer to produce an output of the system 100. The output might be forwarded over the input interface to the ordering instance R or might be outputted via user interface UI to the user again. Also both modalities for outputting the result might be applied. Additionally, the output might be forwarded to a printer to have it in paper form and possibly might be forwarded to a storage resource, such as the database DB or to any other repository or hard disc drive for storing and retrieving data.

The invention further provides another solution which is to be seen in a modification of a conventional test machine T, known in the state of the art. In this case a software module and/or a hardware module, adapted to implement the system 100 according to the present invention is/are incorporated into the test machine T.

With respect to FIG. 2 the flowchart according to the method will be described hereinafter more detailed. However, this flowchart has to be construed as being an example of a possible workflow and might be modified respectively.

In a first step meta-data are provided. Meta-data might refer to historical or actual anamnesis data for the patient, administrative data with respect to the patient, medical personal data for the patient's treatment, meta-data with respect to the patient, like sex, age, family, treatment history etc. Meta-Data, therefore, might refer to the patient, to testing conditions and/or to the treatment context of the patient.

Figure 2:
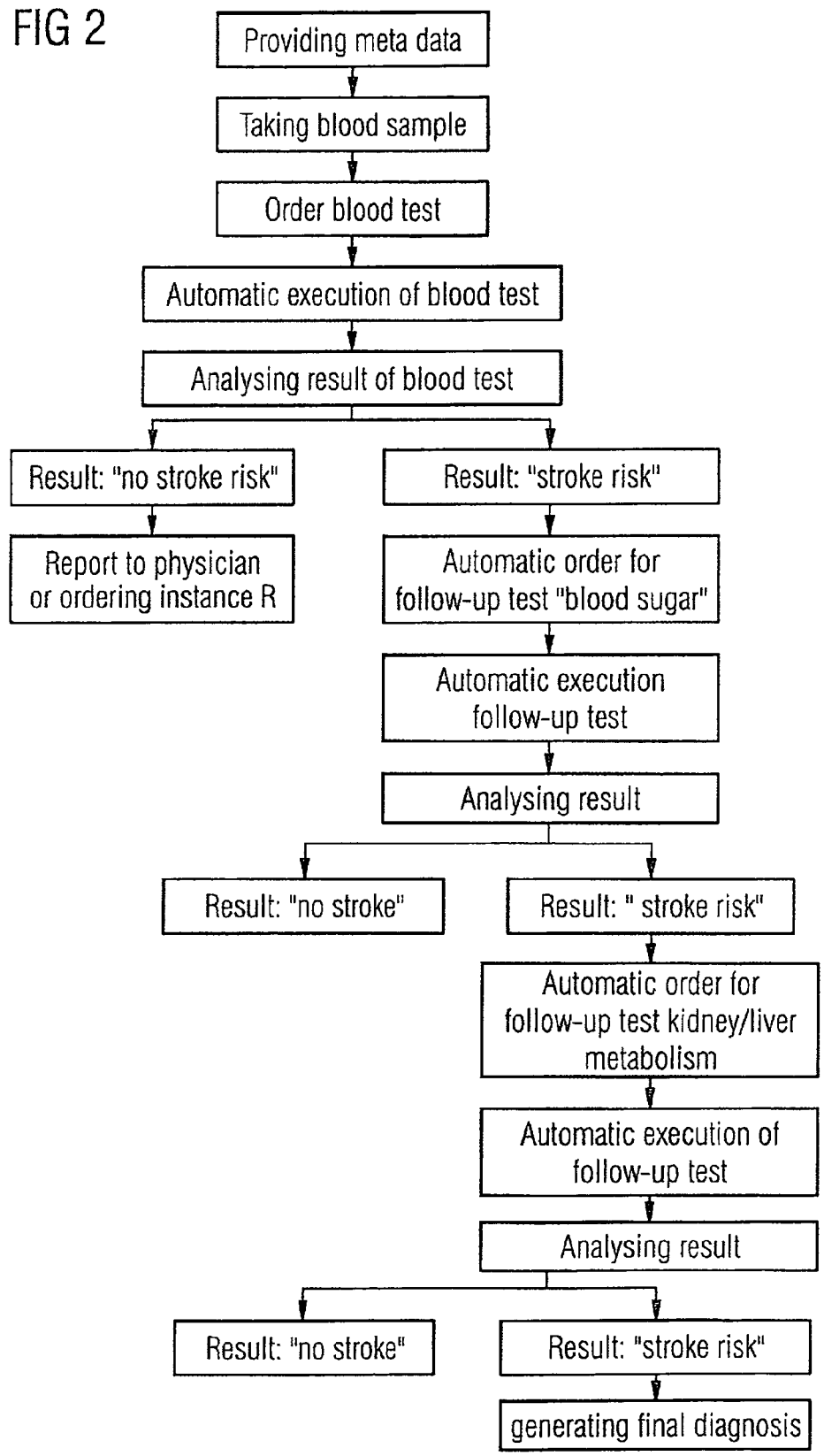

In case a blood test needs to be carried out a blood sample will be taken, which is depicted in FIG. 2 as second step.

After having taken the blood sample, in a third step, the order for the blood test is generated by the ordering instance R.

In a fourth step there is an automatic execution of the ordered blood test. The order for the test is received by the reception unit 10 and was forwarded to the test machine T by means of execution unit 12.

After having executed the blood test the result of the blood test is analyzed in a fifth step. If the result indicates that there is no stroke risk, the result is reported to the ordering instance R, which is depicted on the left hand side on FIG. 2. Otherwise, in case the result indicates a stroke risk, there are automatically deduced further actions to be taken for further treatment of the patient. These further action might be a follow-up test, a report to the physician, the initiation of other clinical actions or a combination thereof.

In the example, depicted in FIG. 2 there needs to be carried out a follow-up test for testing "blood sugar". Then, the order for the (first) follow-up test will be automatically generated. Further, the (first) follow-up test will be executed automatically by the test machine T. After having executed the (first) follow-up test, the result is analyzed within the system 10 again. In case the result indicates no stroke risk, the result will be reported to the physician, as explained above. Otherwise, if the result indicates a stroke risk, a further (second) follow-up test will be automatically ordered. For example a further (second) follow-up test might be directed to testing "kidney/liver metabolism". The order for the second follow-up test will be forwarded to the test machine T, so that the test machine T will automatically execute the further (second) follow-up test. The further follow-up test will then be received by the system 100 again for analyzing the same. Depending on the result of the further follow-up test further actions differ respectively. If the result indicates that there is no stroke risk, then the result will be reported to the physician or to the ordering instance R as being depicted on the left hand side of FIG. 2. Otherwise, if the result indicates a stroke risk, there might be generated a final diagnosis. Usually, a final diagnosis might be executed after having sent the result of the further follow-up test to the physician, so that the physician may decide for one of three alternatives: "No stroke", "Bleeding stroke" and "Ischamic Stroke". These threes alternative diagnoses will lead to alternative treatments for the patient.

As can be seen in FIG. 2 there is a qualified decision for taking further actions in a testing environment, based on the result of the respective predecessor test. Depending on the result of a test, there will be a decision for initiating further steps. Further steps might be seen in initiation and execution of a follow-up test, initiation and execution of a set of follow-up tests, a report to the ordering instance, a report to the treating physician or forwarding the results to another clinical instance.

In the example, depicted in FIG. 2 the ordering physician only generates a "simple" or basic order for a blood test. This order only contains the information "Blood Test". No further conditions and requirements are given. In another example the ordering physician might generate a more complex order. In the latter case the order might comprise additional information. Additional information might be seen in meta-information with respect to the test, parameters for testing, conditions for follow-up tests or a combination thereof. For example it might be possible that the ordering physician generates a conditioned order, like: "Execution of blood test. In case that the result of blood test="Stroke Risk"→follow-up test "Blood Sugar" has to be carried out automatically".

In case of conditioned ordering, the order comprises conditions for executing follow-up tests. A level for specifying the set of follow-up tests might be set dynamically. With other words the user might only initiate one level of further testing, i.e. one follow-up test, depending on the result of the respective predecessor test. Alternatively, it may also specify a second level of testing, i.e. specifying a further and second follow-up test, after having executed the follow-up test and depending on the result of the follow-up test. With other words, this sequence of steps comprising automatic generation of the order, automatic execution of the test, which has been ordered and automatic analyzing of the result of the executed test may be executed iteratively, so that several levels of testing might be initiated and executed automatically.

The system 100 will be monitored, so that the database DB might be updated respectively. As mentioned above, the preferred embodiment relates to the execution of laboratory tests by means of the test machine T. However, any kind of clinical examinations and respective follow-up examinations lie within the scope of this invention. The rules which might be accessed during analyzing will be updated according to recent cases. New rules might be incorporated into the rule database. New rules might be incorporated upon confirmation by a physician before entering the database DB.

A system 100 according to the invention might directly be integrated into an automated IVD-Analyzer T so that a decision for follow-up tests can be made before the blood sample leaves the analyzer.

According to a preferred embodiment the system 100 on-line calculates cost efficiency of follow-up tests, based on the database DB, which also accesses cost-related information and experiences from former tests.

The above description of illustrated embodiments of the invention is not intended to be exhaustive or to limit the invention to precise forms disclosed. While specific embodiments of, and examples for, the invention are described herein for illustrative purposes various equivalent modifications are possible within the scope of the invention and can be made without a deviating from the spirit and scope of the invention.

Further, the method might be implemented in software, in coded form. Alternatively, it is possible to implement the method according to the invention in hardware or hardware modules. The hardware modules are then adapted to perform the functionality of the steps of the method. Furthermore, it is possible to have a combination of hardware and software modules.

These and other modifications can be made to the invention with regard of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

The invention claimed is:

1. A computer implemented method for implementing a set of tests, the method comprising:
    receiving an order for at least one test;
    determining a workflow for the at least one test based on one or more events or results, the workflow including one or more rules, the rules indicate one or more testing conditions, the one or more testing conditions indicating if at least one follow-up test is to be executed;
    automatically executing the received at least one test;
    receiving a result of the executed at least one test;
    analyzing, by a computer processor, the result to determine whether the at least one follow-up test needs to be executed and if yes:
        automatically generating an order for the at least one follow-up test without additional interaction from an entity the order for the at least one test is received from, and
        iteratively executing the steps for the at least one follow-up test.

2. The computer implemented method according to claim 1, wherein at least one of the tests of the set of tests and the follow-up test are based on different clinical departments.

3. The computer implemented method according to claim 1, wherein at least one of the test and the follow-up test of the set of tests are based on the same or on different samples.

4. The computer implemented method according to claim 1, wherein analyzing the result is based on aspects selected from the received result of the respective predecessor test, medical meta information, medical knowledge, definable in rules, and user input.

5. The computer implemented method according to claim 1, wherein applying the steps iteratively for at least one follow-up test includes automatically executing the test, receiving the result for the test, and analyzing the result.

6. The computer implemented method according to claim 1, wherein one of the at least one follow-up test is executed automatically and prior to executing the at least one follow-up test a user confirmation is received.

7. The computer implemented method according to claim 1, wherein executing one of the received at least one test and the at least one follow-up test is done one of immediately after having received the order, at a pre-definable and selectable time schedule.

8. The computer implemented method according to claim 1, wherein the at least one test and the at least one follow-up test are executed in parallel.

9. The computer implemented method according to claim 1, wherein the result of at least one of the at least one test and of the at least one follow-up test are fed back.

10. A computer implemented method for implementing a workflow for tests, the method comprising:
    receiving an input;
    based on the received input, deriving at least one test;
    determining a workflow for the at least one test based on one or more events or results, the workflow including one or more rules, the rules indicate one or more testing conditions, the one or more testing conditions indicating if at least one follow-up test is to be executed;
    automatically executing the at least one test;
    receiving a result of the executed at least one test;
    analyzing, by a computer processor, the result in order to determine whether the at least one follow-up test needs to be executed for responding to the input without additional interaction from an entity the input is received from;
    for the at least one follow-up test iteratively executing the steps:
        automatically starting, receiving the result, analyzing, thereby implementing a workflow as a result-based cascade of tests, wherein a respective test are dependent on a respective result of a respective predecessor test.

11. A computer implemented system for implementing a set of tests, the system comprising:
    a reception unit to receive an order for at least one test;
    an execution unit to execute the received at least one test by means of a test machine;
    a rules module to determine a workflow for the at least one test based on one or more events or results, the workflow including one or more rules, the rules indicate one or more testing conditions, the one or more testing conditions indicating if at least one follow-up test is to be executed;
    an analyzing module to receive a result of executed at least one test and adapted for analyzing the result in order to determine whether the at least one follow-up test needs to be executed;
    an iteration unit to generate an order for an at least one follow-up test without additional interaction from an entity the order for the at least one test is received from, in case such a follow-up test needs to be executed and forwarding the order for the at least one follow-up test to the reception unit.

12. A test machine for executing clinical tests, comprising a computer implemented system according to claim 11.

13. A non-transitory memory including computer readable instructions stored therein, the instructions causing the computer processor to perform the steps of the method according to claim 1 when the instructions are executed on the computer processor.

* * * * *